(12) United States Patent
Johnson

(10) Patent No.: US 10,614,696 B2
(45) Date of Patent: Apr. 7, 2020

(54) STERILE WET PACK DETECTOR SYSTEM

(71) Applicant: Winston Johnson, Jeffersonville, IN (US)

(72) Inventor: Winston Johnson, Jeffersonville, IN (US)

( * ) Notice: Subject to any disclaimer, the term of this patent is extended or adjusted under 35 U.S.C. 154(b) by 0 days.

(21) Appl. No.: 16/029,580

(22) Filed: Jul. 7, 2018

(65) Prior Publication Data
US 2019/0188989 A1   Jun. 20, 2019

Related U.S. Application Data

(60) Provisional application No. 62/607,410, filed on Dec. 19, 2017.

(51) Int. Cl.
G08B 21/00 (2006.01)
G08B 21/18 (2006.01)
G01N 33/00 (2006.01)

(52) U.S. Cl.
CPC ....... *G08B 21/182* (2013.01); *G01N 33/0031* (2013.01)

(58) Field of Classification Search
CPC .............................. G08B 21/182; D06F 58/28

USPC .......... 340/602, 604, 611, 614; 34/487, 496, 34/499, 535, 562
See application file for complete search history.

(56) References Cited

U.S. PATENT DOCUMENTS

| | | | | |
|---|---|---|---|---|
| 5,649,372 A * | 7/1997 | Souza | ..................... | D06F 58/28 34/491 |
| 6,122,840 A * | 9/2000 | Chbat | ..................... | D06F 58/28 34/496 |
| 2007/0154344 A1* | 7/2007 | Choi | ....................... | A61L 9/015 422/3 |
| 2012/0144692 A1* | 6/2012 | Park | ....................... | D06F 58/04 34/491 |
| 2018/0280553 A1* | 10/2018 | Leupold | ................. | C12M 37/00 |

* cited by examiner

*Primary Examiner* — Tai T Nguyen
(74) *Attorney, Agent, or Firm* — Malone IP Law; Steven J. Malone

(57) ABSTRACT

A system and method for indicating dryness of a sterilizer product includes taking a first humidity reading before a cycle of the sterilizer is started, taking a second humidity reading after the cycle of the sterilizer is finished, indicating to a user the dryness of the sterilizer product based on the first humidity reading and the second humidity reading.

9 Claims, 8 Drawing Sheets

STERILE WET PACK DETECTOR SYSTEM

RELATED APPLICATIONS

This application claims priority to a U.S. provisional application 62/607,410 titled "Sterile Wet Pack Detector System" filed on Dec. 19, 2017 and is hereby incorporated by reference, in its entirety, for all it discloses and conveys.

FIELD OF THE INVENTION

The present invention relates generally to humidity sensing and more specifically to a humidity sensor system that detects humidity being emitted from a sterilizer chamber after completion of a sterile cycle.

BACKGROUND

In health care, a hospital central processing department is responsible for sterilizing surgical instruments in preparation for use in surgical procedures. These instruments are cleaned, disinfected, wrapped and sterilized. Common problems associated with sterilization of wrapped packs of surgical instruments include: verification of a proper sterile cycle and verification of proper surgical pack humidity conditions within the surgical pack at the end of the sterile cycle. The sterilization process uses steam which may condense creating a potentially problematic wet-pack environment within the surgical pack at the end of a sterile cycle. When sterile packs are opened in a surgery setting, any sign of moisture within a surgical pack is interpreted as an unsterile condition and the instruments cannot be used. The unsterile instruments are considered unfit and must be reprocessed. When wet-packs are found, surgical procedures may be delayed, prolonged, or canceled.

SUMMARY

A system and method for indicating dryness of a sterilizer product includes taking a first humidity reading before a cycle of the sterilizer is started, taking a second humidity reading after the cycle of the sterilizer is finished, and indicating to a user a dryness of the sterilizer product based on the first humidity reading and the second humidity reading.

The method may include taking the first humidity reading as a result of pushing a button. The method may include storing the first humidity reading as a baseline humidity reading as a result of pushing the button. The indication of the dryness may be a difference between the first humidity reading and the second humidity reading. The indication of the dryness may be accomplished by turning on a red light or a green light based on a difference between the first humidity reading and the second humidity reading. The indication of the dryness of the sterilizer products may be accomplished by displaying to a user the first humidity reading and the second humidity reading. The first humidity reading may be a result of one or more humidity samples before the cycle of the sterilizer is started. The second humidity reading may be a result of one or more humidity samples after the cycle of the sterilizer is finished. The indication of the dryness may be accomplished by sounding an alarm based on a difference between the first humidity reading and the second humidity reading. An alarm may be sounded when the difference is more than a predetermined threshold. A sterilizer may include a sterilizer dryness device attached to the sterilizer, the sterilizer dryness device may include at least two humidity sensors, a micro-processor, at least one humidity sample trigger, and an indicator for indicating a dryness of a product of the sterilizer. The sterilizer may include a motion sensor to trigger one or more samples. The indicator may be a display, an alarm, an indicator light, or a combination thereof. The sterilizer may further comprise one or more valves. The sterilizer may further comprise one or more fans. The sterilizer may further comprise one or more vacuum generators. The sterilizer may further comprise one or more indicator lights. The sterilizer may further comprise one or more powers supplies. The sterilizer may further comprise a door lock. The sterilizer may further comprise a steam quality system which calculates an input steam quality based on temperature and pressure of the input steam into the sterilizer.

The present invention will detect the humidity being emitted from the sterilizer chamber after completion of a sterile cycle. The present invention will give the operator of the sterilizer a visual comparison of the humidity outgassing from sterilizer chamber and compare it with the room set valve entered before sterilizer door was open (by pressing set button). The present invention can also be interfaced with sterilizers using solenoid valve connected to an air inlet valve with piping, sampling internal humidity. This may be accomplished by a vacuum produced by two 40 mm fans located at the top of enclosure. These two fans will pull humidity into the present invention and the sampling of humidity from piping connected to sterilizer. Then it will compare sampled humidity with the threshold (starting internal humidity). It can also sample the open-door humidity emissions and compare it to the staring set value before door was opened. Humidity, may be sensed by two SHT11 sensors and using an Arduino microprocessor. Sensor readings may be processed and display on a Nextion 3.2" display. The display may show set-humidity (start humidity) and present humidity emissions from the load. Sampling may also be accomplished by opening door and monitoring humidity emissions and comparing it to a staring set value before the door was opened. Sample humidity is pulled into bottom of control enclosure through vents. Using same 40 mm fans and processed as for mentioned. For the enclosure and wiring, there is a LCD or LED display that shows the set-value (starting value) humidity and chamber humidity. When starting humidity and chamber humidity are the same or close, the operator will then remove sterile packs/instruments from sterilizer. This will provide another level of assurance that the sterile load is not wet.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings.

Figure 1:
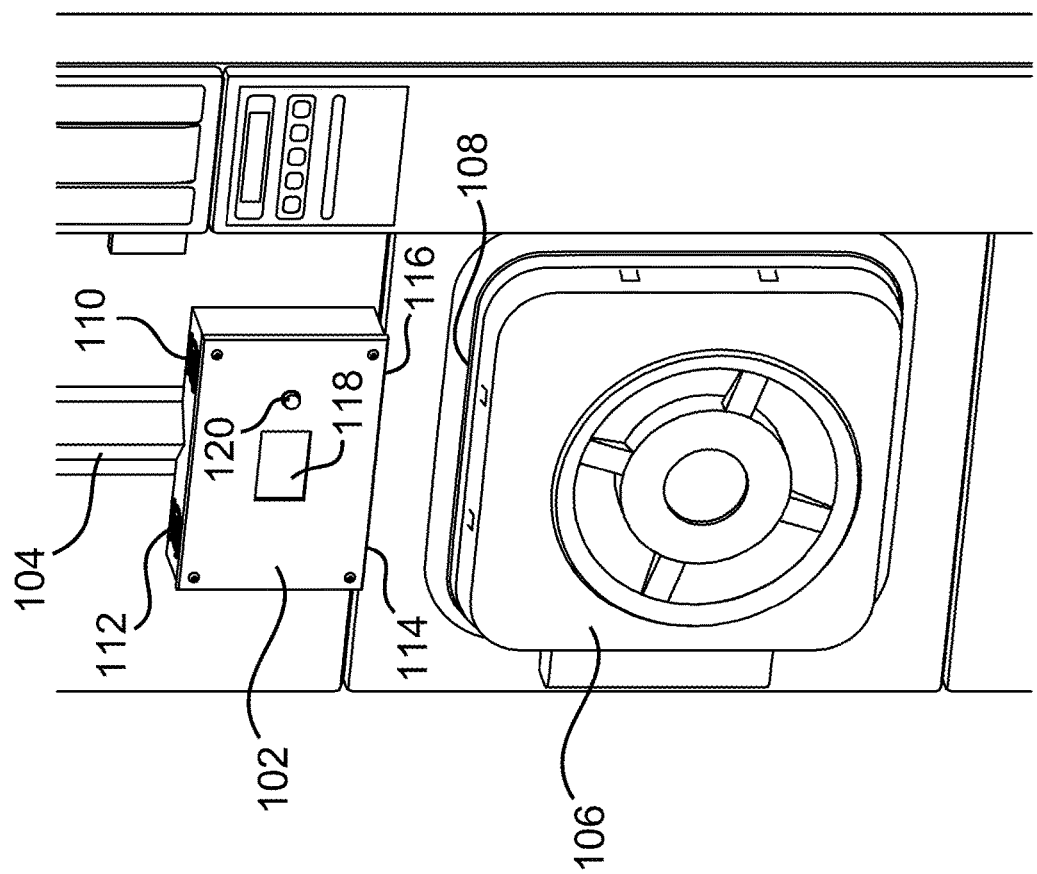
FIG. 1 shows a closed sterilizer in accordance with an embodiment of the invention.

In FIG. 1, a sterilizer 100 includes a humidity device 102 attached above the sterilizer door 106. The humidity device 102 may include a mount 104 for attaching or mounting humidity device 102 to sterilizer 100. Mount 104 may be a hanger, bracket or other attachment device for attaching humidity device 102 to sterilizer 100. Door 106 may open at or near opening 108 allowing an internal humidity level to be detected by humidity detector 102. Humidity detector 102 may be used to detect mechanical or electrical problems with sterilizer 100. At the completion of a sterile cycle, humidity inside of the sterilizer and humidity outside of the sterilizer should be equal or nearly the same. If sterilizer 100 short cycles due to operator control or has a mechanical and/or electrical problem, humidity detector 100 can alert an operator of a wet pack condition. Wet packs of surgical instruments are not considered sterile and cannot be safely used in a surgical procedure. Humidity detector 102 may include one or more humidity input ports 114/116 and one or more humidity output ports 112/110. Humidity detector 102 may also include local and remote humidity sample triggers and/or indicators 120. Sterilizer 100 may additionally include a printer, memory, or remote storage device for logging, displaying, or printing humidity readings, temperature readings, pressure readings, differential humidity readings, differential temperature readings, differential pressure readings, or combinations thereof. Logged data may indicate to a user of sterilizer 100 that the sterilizer cycle was completed within normal or abnormal operating conditions and whether the instruments within the sterilizer meet minimum acceptable sterilization standards. A processor within sterilizer device 102 or a remote computer may assign a batch number or processing number to a sterile cycle lot (batch of surgical instruments sterilized together) and report the logged data including data falling inside and outside of acceptable ranges to a remote database server or other printer or memory device of sterilizer 100. Report of a completed sterile cycle may be transmitted by text, SMS, email, push notification, and/or other audio, visual, or tactile device to inform a user of the result of the sterile cycle.

Figure 2:
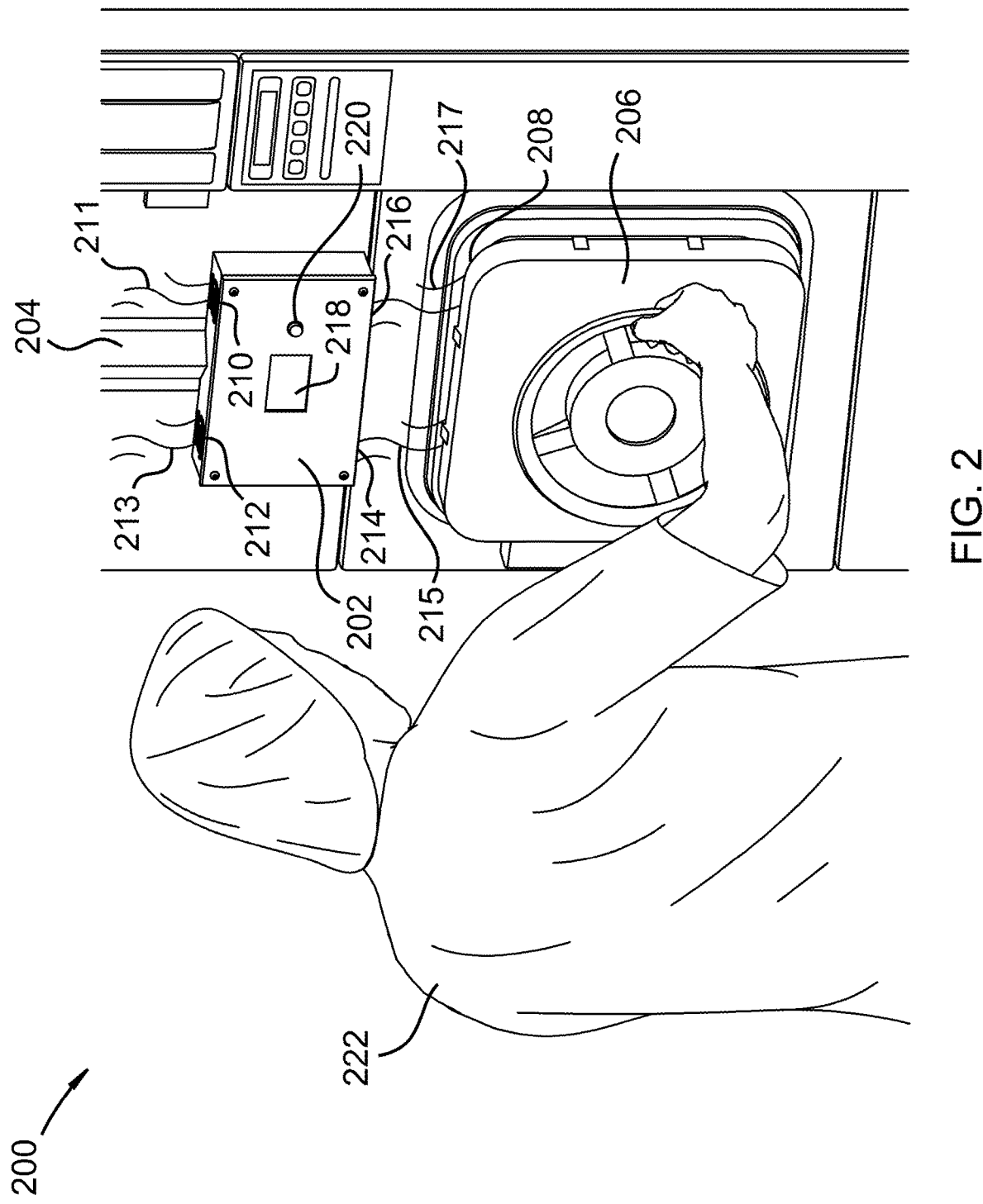
FIG. 2 shows an open sterilizer in accordance with an embodiment of the invention.

FIG. 2 shows a sterilizer 200 including a humidity device 202 attached above the sterilizer door 206. The humidity device 202 may include a mount 204 for attaching or mounting humidity device 202 to sterilizer 200. Mount 204 may be a hanger, bracket or other attachment device for attaching humidity device 202 to sterilizer 200. Door 206 may open at or near opening 208 allowing an internal humidity level 215/217 to be detected by humidity detector 202. Humidity detector 202 may be used to detect mechanical or electrical problems with sterilizer 200. At the completion of a sterile cycle, humidity inside of the sterilizer 215/217 and humidity outside of the sterilizer should be equal or nearly the same. If sterilizer 200 short cycles due to operator 222 control or has a mechanical and/or electrical problem, humidity detector 200 can alert an operator 222 of a wet pack condition. Wet packs of surgical instruments are not considered sterile and cannot be safely used in an operation. Humidity detector 202 may include one or more humidity input ports 214/216 and one or more humidity output ports 212/210. Humidity detector 202 may also include local and remote humidity sample triggers and/or indicators 220. In one example, operator 222 approached sterilizer 200 and desires to end a sterile cycle early. Operator 222 then triggers or takes a sample humidity reading by pushing a local 220 sample button or a remote sample button on the floor (not shown) while door 206 is closed. When the closed-door humidity reading is obtained, operator 222 may open door 206 and trigger a second open-door humidity reading representative of a humidity within sterilizer 200. Operator may then determine that the readings are equal or within a predetermined threshold of each other leading to a conclusion that the surgical packs within sterilizer are dry. If, on the other hand, the humidity readings are not equal or within a predetermined threshold, a conclusion can be made that the surgical packs are wet and not safe to use. Humidity readings outside of a proper range may indicate the sterile cycle was prematurely ended or that the sterilizer has a mechanical and/or electrical problem. An indicator may be used to notify an operator or maintenance person if a sterile cycle was prematurely ended or if maintenance is needed. Various humidity threshold range deviations may be correlated with and be used to indicate specific sterilizer problems. Sterilizer 200 may additionally include a printer, memory, or remote storage device for logging, displaying, or printing humidity readings, temperature readings, pressure readings, differential humidity readings, differential temperature readings, differential pressure readings, or combinations thereof. Logged data may indicate to a user of sterilizer 200 that the sterilizer cycle was completed within normal or abnormal operating conditions and whether the instruments within the sterilizer meet minimum acceptable sterilization standards. A processor within sterilizer device 202 or a remote computer may assign a batch number or processing number to a sterile cycle lot (batch of surgical instruments sterilized together) and report the logged data including data falling inside and outside of acceptable ranges to a remote database server or other printer or memory device of sterilizer 200. Report of a completed sterile cycle may be transmitted by text, SMS, email, push notification, and/or other audio, visual, or tactile device to inform a user of the result of the sterile cycle.

Figure 3:
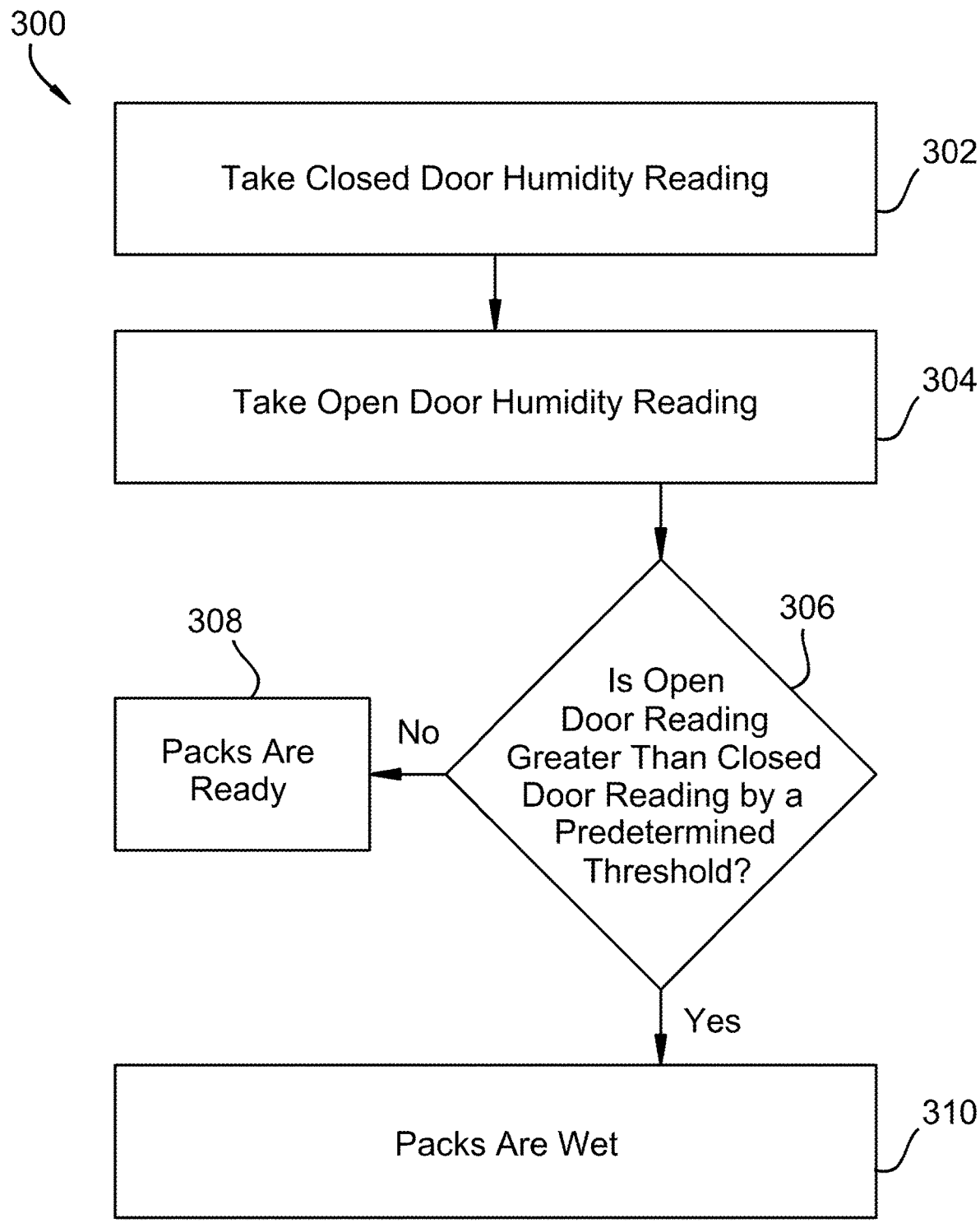
FIG. 3 shows a flow chart of a method in accordance with an embodiment of the invention.

FIG. 3 shows a flow chart of a method 300 in accordance with an embodiment of the invention. At step 302, a closed-door humidity reading is taken. This reading may be triggered by a motion sensor, a push button, or a proximity sensor. At step 304, an open-door humidity reading is taken. This reading may be manually or automatically triggered as the door is opened. A door switch, motion sensor, proximity sensor, or manual button may be used to trigger the sampling of humidity exiting from within the sterilizer as the sterilizer door is opened. At step 306, a determination is made based on the open-door read and the closed-door reading. If the readings are within a predetermined threshold, such as 5% or less, then the packs are ready and dry 308. If the readings are outside of a predetermined threshold, such as above 5%, then the packs are wet 310 and cannot be used. The predetermined threshold setting may be set by an operator or maintenance person and may be adjusted based on normal humidity variability within a specific room, region, or area.

Figure 4:
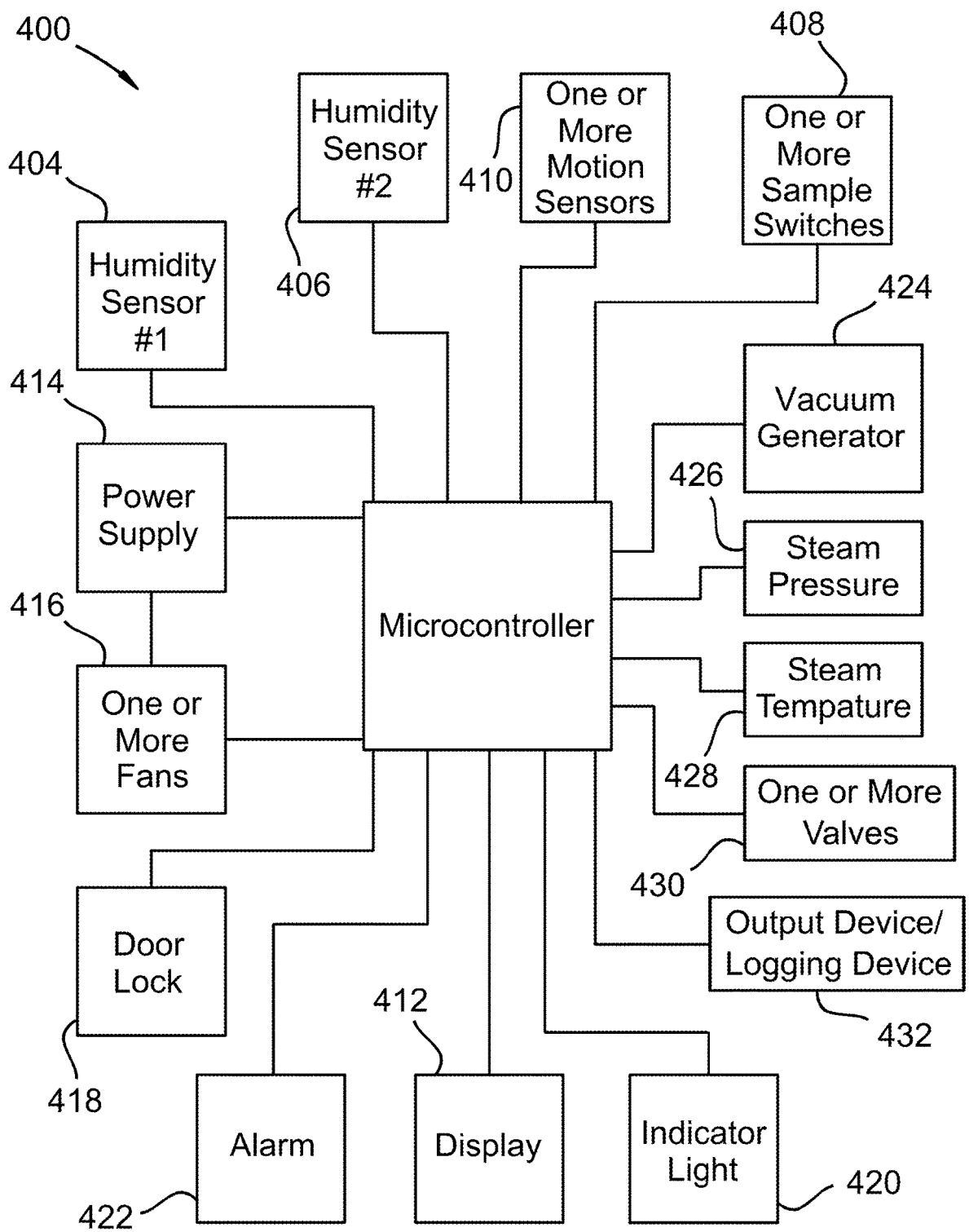
FIG. 4 shows a diagram of humidity detector options in accordance with embodiments of the invention.

FIG. 4 shows a diagram 400 of humidity detector options in accordance with embodiments of the invention. In one embodiment, components of diagram 400 may be internal to a sterilizer machine and factory installed when the sterilizer was originally built. In another embodiment, some or all of the components of diagram 400 are retrofitted to an existing sterilizer machine. Microprocessor 402 may be a microcontroller with analog inputs, digital inputs, relay output, high voltage inputs and outputs or any other type of microprocessor/microcontroller including Arduino, Raspberry Pi, embedded processors, application specific integrated circuits, micro-logic controllers, computer processors, cell phone processors, iPad processors, tablet processors, etc. Humidity sensors 404/406 may be any type of humidity sensor including resistive, inductive, reactive, capacitive, image based, and/or spectrographic. While two humidity sensors 404/406 are shown, more than two may be used and in some embodiments multiple humidity sensor readings may be averaged. Multiple humidity readings from the same humidity sensor and/or multiple humidity readings from multiple sensors may be averaged or integrated over time. Sample switches 408 may include motion sensors, timed switching relays, push buttons, switches, and/or proximity sensors. Motion sensors 410 may be located on a humidity detection device, on a sterilizer machine, or near a door of a sterilizer machine. Display 412 may be an LED display, LCD display, indicator, monitor, or any other display device. Power supply 414 may provide power to microprocessor 402, one or more fans 416, vacuum generator 424, sensors 410/404/406, display 412, alarm 422, indicator lights 420, door lock 418, and any other device used with the humidity detector. One or more valves 430 may be used to vent steam, isolate an inner area of a sterilizer from an outer area around the sterilizer, sample steam, read temperatures inside and outside of a sterilizer, read pressures inside and outside of a sterilizer, read pressures inside and outside of a steam line, read saturation of incoming steam, or any combination thereof. Pressure sensors 426 may be used to read pressure in a supply steam line, within a sterilization chamber, and/or within a boiler chamber of a sterilizer. Temperature sensors 428 may be used to read temperatures in a supply steam line, within a sterilization chamber, around an outside area of a sterilizer and/or within a boiler system of a sterilizer. Output logging device 432 may be a printer, display, LEDs, audible alarms, electronic notification systems such as texting systems, SMS systems, email systems, computer systems, and/or database server systems. Output logging device 432 may indicate to a sterilizer operator or to another hospital quality control person results of each sterilizer cycle and any out-of-normal conditions associated with temperature, pressure, steam quality, humidity levels, and pass/fail data information on each sterilizer lot. Microprocessor/microcontroller 402 may determine if a sterilizer cycle meets minimum requirements for a successful sterilization process before unlocking a lock on the sterilizer. An unlock code may be required to open the sterilizer if it fails thus providing a second level of authorization when a sterilizer cycle fails. An incoming steam supply line may be monitored by microprocessor/microcontroller 402 to determine if the incoming steam is within proper steam temperature/pressure levels for a sterilizer to function properly. If input steam is outside of normal conditions, microcontroller may cause steam to vent until acceptable steam conditions are present before starting a sterilizer cycle. Sterilizer cycle monitoring may include logging all parameters of temperature, pressure, steam quality, and time throughout a sterilizer cycle to insure the sterilizer is functioning within set quality parameters.

Figure 5:
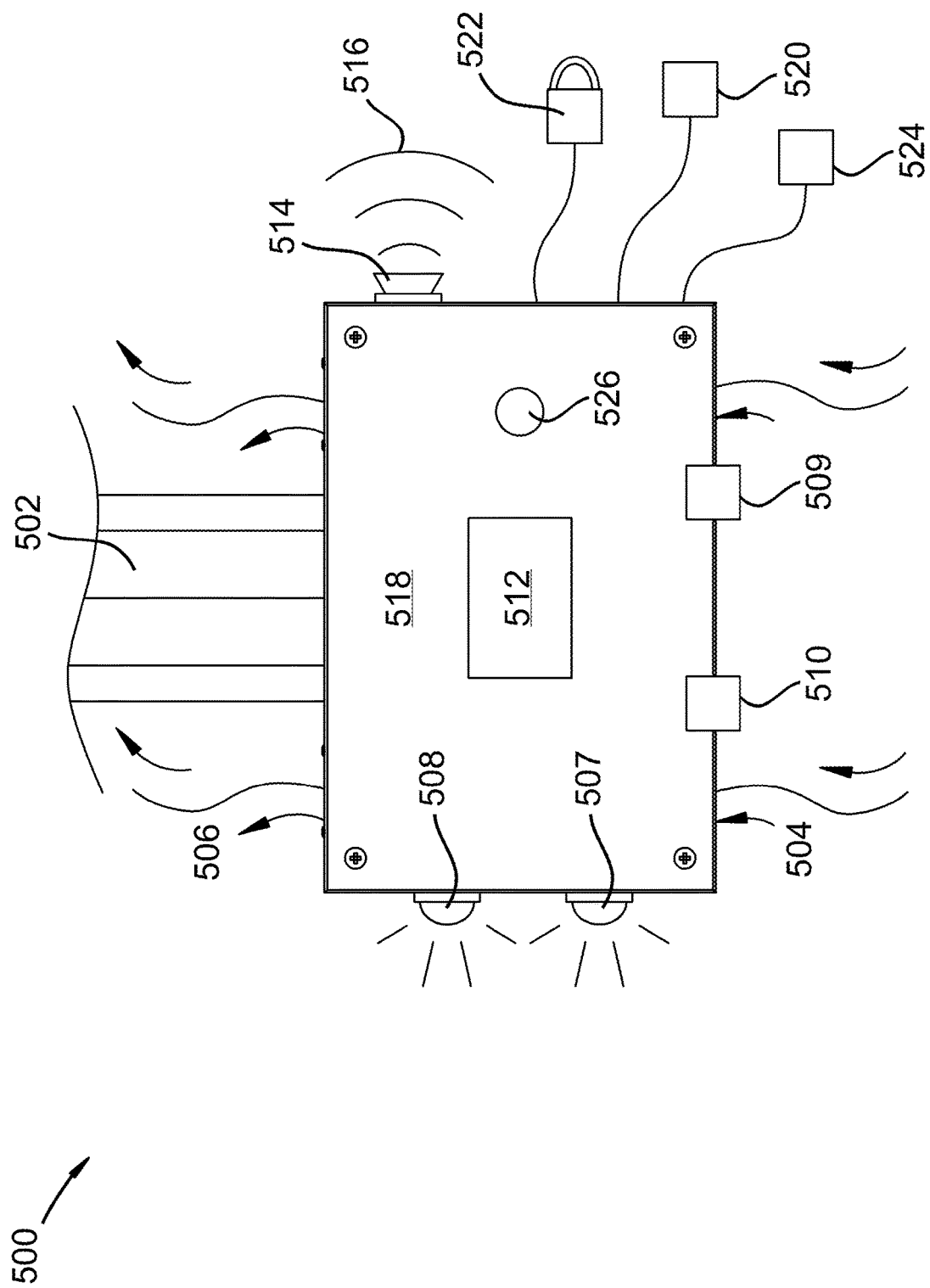
FIG. 5 shows a diagram of humidity detector options in accordance with embodiments of the invention.

FIG. 5 shows a diagram 500 of humidity detector options in accordance with embodiments of the invention. Humidity detector 518 may use fans 416 (FIG. 4) to draw air from a bottom side 504 to a top side 506 of humidity detector 518. Motion sensors 510/509 may be mounted directly to humidity detector 518 or may be remote from the enclosure 518. Motion sensors 510 and 509 may be angled to sense motion in different regions of space. For instance, sensor 509 may be angled to receive movement from a door of a sterilizer while sensor 510 may be angled to receive movement of an operator approaching a sterilizer machine. Sensor 510 may trigger a closed-door humidity sample reading as the operator approaches the sterilizer and sensor 509 may trigger a closed-door humidity reading after the operator opens the door of the sterilizer. Audio/visual indicators 507/508 and/or 514 may be activated as a result of a wet pack detection or dry pack detection. A green light may indicate the pack or packs are dry while a red light may indicate that packs are wet. An audible alarm 514 may sound if wet packs are detected to alert the operator of wet packs. A door lock 522 may be enabled if the packs are wet and disabled if the packs are dry. Remote sensors/switches 520/524 may be used to remotely sample humidity and to remotely trigger humidity sampling.

Figure 6:
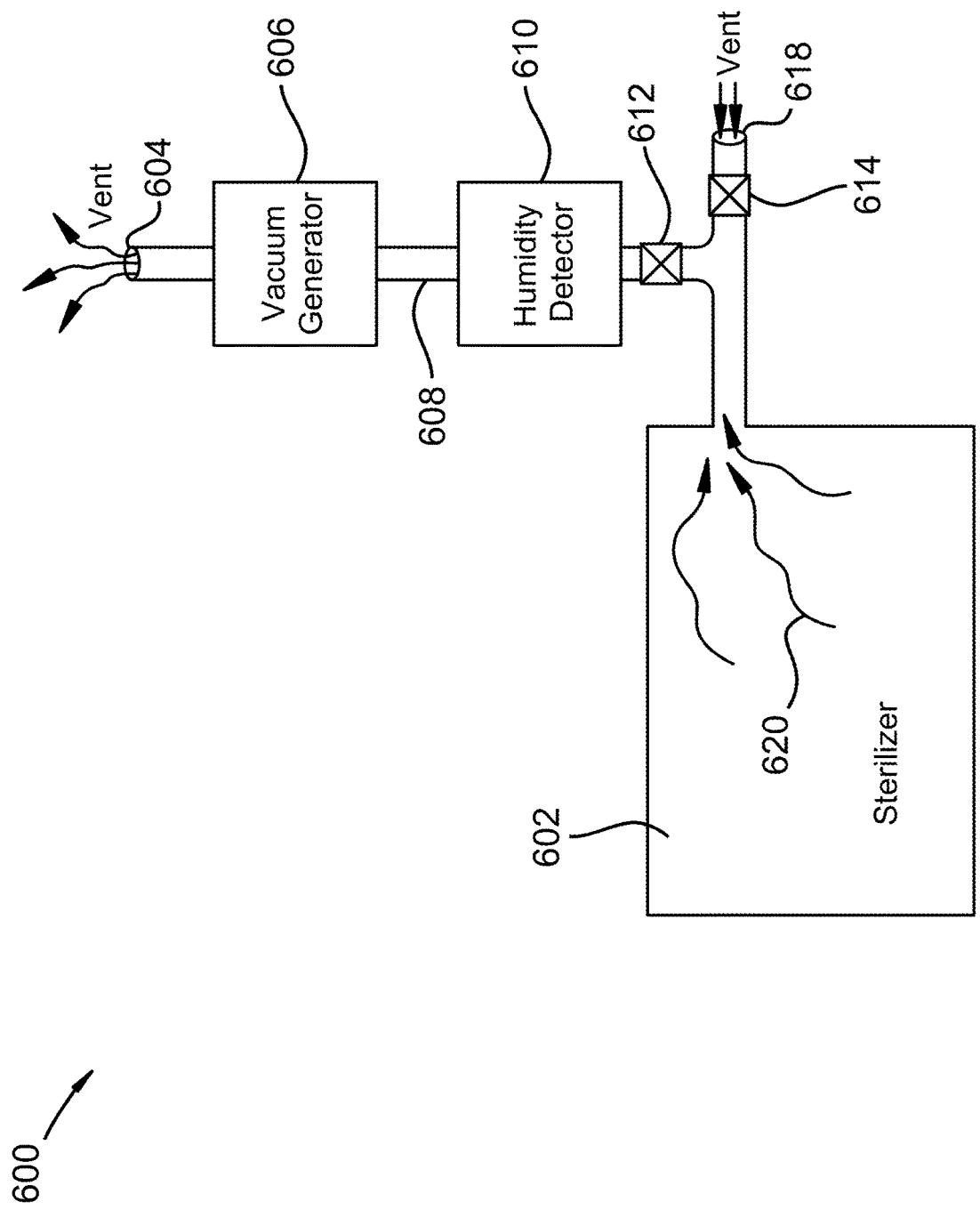
FIG. 6 shows a diagram in accordance with an embodiment of the invention.

FIG. 6 shows a sterilizer 602 with a venting system designed to sample humidity inside of sterilizer 602 and outside of sterilizer 602. At the completion of a sterile cycle, a valve 612 may be opened to take a humidity reading within sterilizer 602. Humidity 620 may be drawn up through humidity detector 610 by a vacuum generator 606 and vented out at 604. Humidity detector 610 may compare an inside humidity to an outside humidity based on a predetermined humidity threshold and determine if packs are wet or dry and give a wetness/dryness indication to an operator of the sterilizer. The predetermined threshold may be set by an operator or maintenance person based on normal humidity variations of a room, area, or region.

Figure 7:
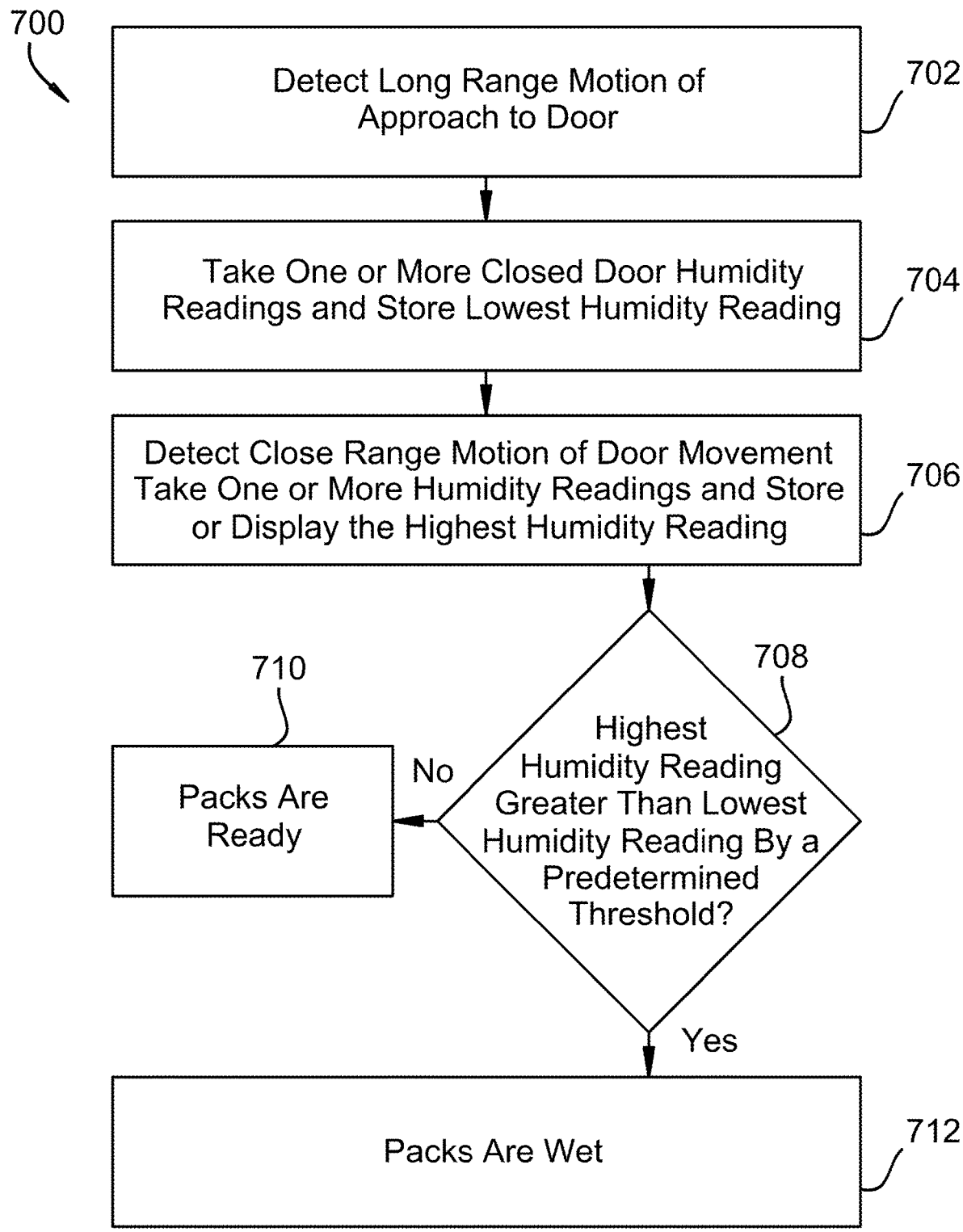
FIG. 7 shows a flow chart of a method in accordance with an embodiment of the invention.

FIG. 7 shows a flow chart of a method 700 in accordance with an embodiment of the invention. At step 702 a long-range motion is detected with a motion detector as an operator approached a sterilizer machine. At step 704, one or more closed-door humidity readings are taken, and the lowest or averaged humidity reading is stored, averaged, and/or displayed. At step 706, a close-range motion is detected with a motion detector as a door of the sterilizer is opened and one or more open-door humidity readings are stored, averaged, and/or displayed. A door switch, motion sensor, proximity sensor, or manual button may be used to trigger the sampling of humidity exiting from within the sterilizer as the sterilizer door is opened. At step 708, a determination is made based on the open-door read and the closed-door reading. If the readings are within a predetermined threshold, such as 5% or less, then the packs are ready and dry 710. If the readings are outside of a predetermined threshold, such as above 5%, then the packs are wet 712 and cannot be used. The predetermined threshold setting may be set by an operator or maintenance person and may be adjusted based on normal humidity variability within a specific room, region, or area.

Figure 8:
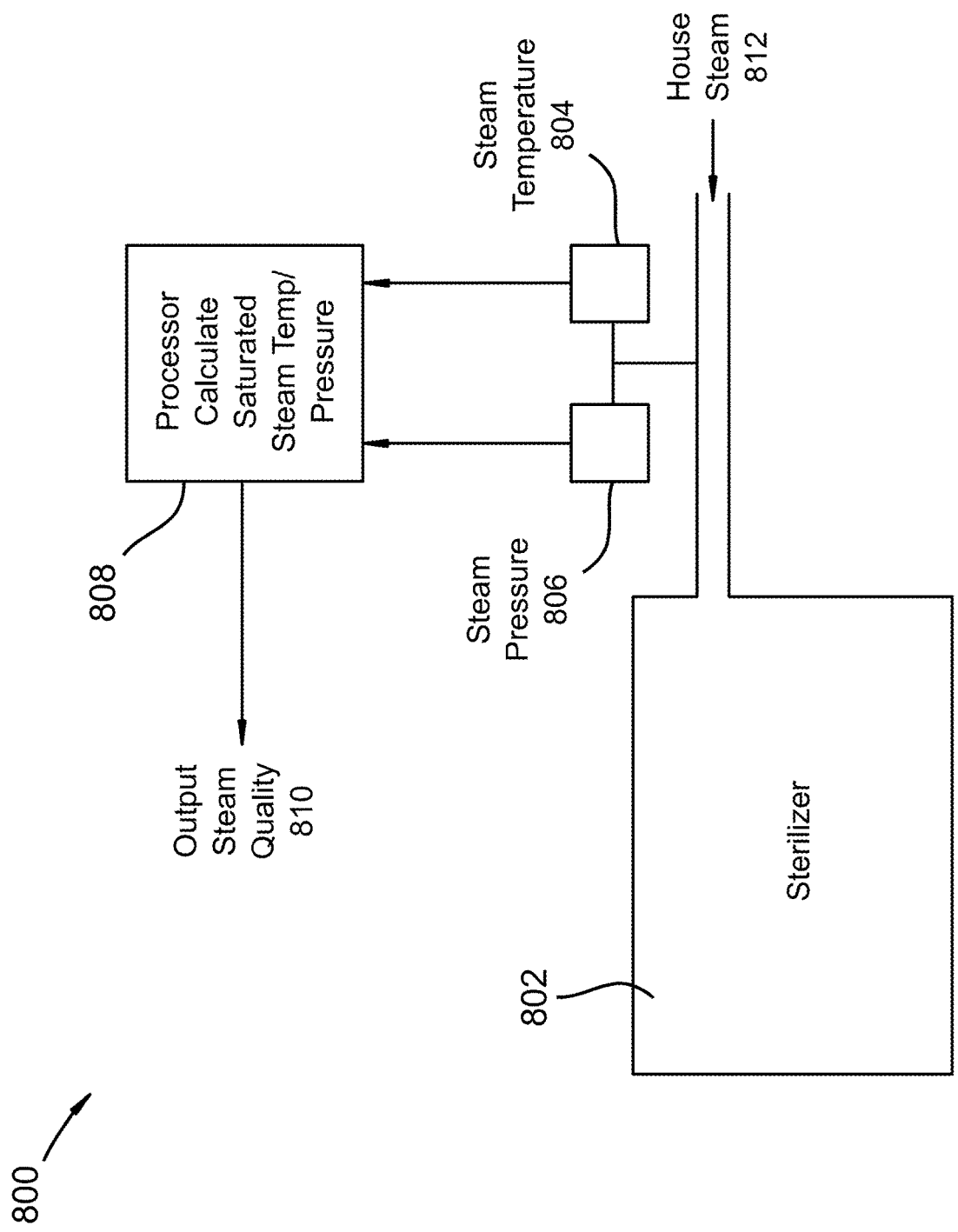
FIG. 8 shows a steam quality sterilizer system in accordance with an embodiment of the invention.

FIG. 8 shows a steam quality sterilizer system 800 in accordance with an embodiment of the invention. A steam quality sterilizer system 800 includes a processor and memory 808, a steam pressure sensor 806, a steam temperature sensor 804, a sterilizer 802, steam input supply 812, and steam quality output device 810. Processor/memory 808 may be the same processor/controller used in the steam dryness detector shown in FIG. 4 or may be a separate microprocessor/micro-controller. Steam pressure sensor 806 may be any suitable pressure transducer useable with steam pressures and steam temperatures. Steam temperature sensor 804 may be a resistive, capacitive, junction, electro-mechanical, or any other available temperature transducer. Pressure and Temperature transducers 806/804 may be connected to an inlet or supply steam line 812. Supply stem line 812 may be house steam supplied from a remote boiler or may be local steam supplied from a boiler within a sterilizer machine. Sterilizer 802 uses steam to sterilize surgical equipment within normal safety control limits. Processor/memory 808 is able to calculate steam quality related to pressure, temperature, and steam saturation and determine if input steam 812 is of good quality, fair quality, marginal quality, or poor quality and report the steam quality to an output quality device 810. Output quality device 810 may be a display, one or more lights, a computer system with notification capabilities, or a database server with programming to report steam quality of each sterile cycle of sterilizer 802 to one or more users, safety systems, compliance systems or hospital personnel. An input-steam or supply steam quality reporting system may report steam quality data to one or more systems, devices, users, or compliance systems. A report for each sterile cycle may be generated detailing steam quality, dryness of surgical instruments, temperatures throughout the cycle, steam quality throughout the cycle, and/or pressures throughout the cycle.

The systems and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A sterilizer for indicating dryness of a sterilizer product comprising:
  a pressure sensor for reading a supply steam pressure in a supply steam line of a sterilization chamber of the sterilizer;
  a temperature sensor for reading the supply steam temperature in a supply steam line of the sterilization chamber of the sterilizer;
  an input steam quality reporting system for reporting a quality of the supply steam;
  wherein the supply steam pressure and the supply steam temperature are used to determine the quality of the supply steam;
  a sterilizer dryness device attached to the sterilizer, the sterilizer dryness device comprising:
    one or more humidity sensors for reading one or more humidity levels within the sterilization chamber;
    a micro-processor;
    at least one humidity sample trigger;
    wherein the micro-processor is configured to determine if a sterilizing cycle meets minimum requirements for a successful sterilization process before unlocking a lock on the sterilizer and is configured to identify a dryness of the sterilizer product based on a comparison of the one or more humidity levels and a humidity sample trigger;
    an indicator for indicating the dryness of the product of the sterilizer; and
    wherein the quality of the supply steam and the dryness of the product of the sterilizer of each sterilizing cycle of the sterilizer are reported to one or more systems, devices, users, or compliance systems.

2. The sterilizer of claim 1, wherein the at least one humidity sample trigger is a push button.

3. The sterilizer of claim 1, wherein the at least one humidity sample trigger is a motion sensor.

4. The sterilizer of claim 1, wherein the indicator is a display, an alarm, an indicator light, or a combination thereof.

5. The sterilizer of claim 1, further comprising one or more fans.

6. The sterilizer of claim 1, further comprising one or more vacuum generators for sampling humidity.

7. The sterilizer of claim 1, further comprising a recording device for recording a humidity associated with the at least two humidity sensors.

8. The sterilizer of claim 7, wherein the recording device is a printer, a memory device, a database, or a combination thereof.

9. The sterilizer of claim 1, further comprising a door lock.

* * * * *